United States Patent
Heinzelman et al.

Patent Number: 5,353,806
Date of Patent: Oct. 11, 1994

[54] LIQUID COLLECTION DEVICE

[75] Inventors: Bert D. Heinzelman, Tenafly, N.J.; Donald R. Lamond, Long Beach, N.Y.

[73] Assignee: The Venture Fund of Washington, Washington, D.C.

[21] Appl. No.: 27,287

[22] Filed: Mar. 4, 1993

[51] Int. Cl.⁵ .............................................. A61B 5/00
[52] U.S. Cl. ........................................ 128/763; 604/52
[58] Field of Search ........................ 128/760, 763–766; 604/32–34, 52, 190, 248, 249; 220/303, 371, 253, 254

[56] References Cited

U.S. PATENT DOCUMENTS

| | | |
|---|---|---|
| 3,141,336 | 3/1961 | Oates. |
| 3,978,846 | 9/1976 | Bailey. |
| 4,024,857 | 5/1977 | Blecher et al. ................ 128/763 |
| 4,050,451 | 9/1977 | Columbus. |
| 4,091,802 | 5/1978 | Columbus. |
| 4,136,796 | 1/1979 | Dubois et al. ................ 220/303 |
| 4,210,156 | 7/1980 | Bennett ........................ 128/763 |
| 4,266,558 | 5/1981 | Akhavi ......................... 128/766 |
| 4,266,559 | 5/1981 | Akhavi ......................... 128/766 |
| 4,317,455 | 3/1982 | Akhavi. |
| 4,327,745 | 5/1982 | Ford, Jr. ...................... 128/765 |
| 4,340,067 | 7/1982 | Rattenborg .................. 128/763 |
| 4,367,754 | 1/1983 | Akhavi ......................... 128/763 |
| 4,378,812 | 4/1983 | Sarstedt ....................... 128/765 |
| 4,385,637 | 5/1983 | Akhavi ......................... 128/763 |
| 4,393,882 | 7/1983 | White ........................... 128/764 |
| 4,396,024 | 8/1983 | Sarstedt ....................... 128/763 |
| 4,552,155 | 11/1985 | Etterington et al. ......... 128/765 |
| 4,589,421 | 5/1986 | Ullman ......................... 128/763 |
| 4,660,569 | 4/1987 | Etherington .................. 128/765 |
| 4,703,762 | 11/1987 | Rathbone et al. ............ 128/763 |
| 4,731,059 | 3/1988 | Wanderer et al. ............ 128/765 |
| 4,805,635 | 2/1989 | Korf et al. .................... 128/763 |
| 4,991,601 | 2/1991 | Kasai et al. .................. 128/763 |
| 5,054,498 | 10/1991 | Melet ........................... 128/763 |
| 5,110,557 | 5/1992 | Brown et al. ................. 128/763 |
| 5,125,415 | 6/1992 | Bell .............................. 128/766 |

Primary Examiner—Max Hindenburg
Attorney, Agent, or Firm—Wolf, Greenfield & Sacks

[57] ABSTRACT

A liquid, preferably blood, collection device including an elongated collection tube having an inlet, an outlet and defining a chamber therebetween for holding the collecting liquid. A rotatable valve cap allows the user to selectively control the introduction of liquid into the device. The cap is removable allowing access to the collected liquid. An annular reservoir containing an additive is provided out of the flow path of the liquid into the tube.

15 Claims, 3 Drawing Sheets

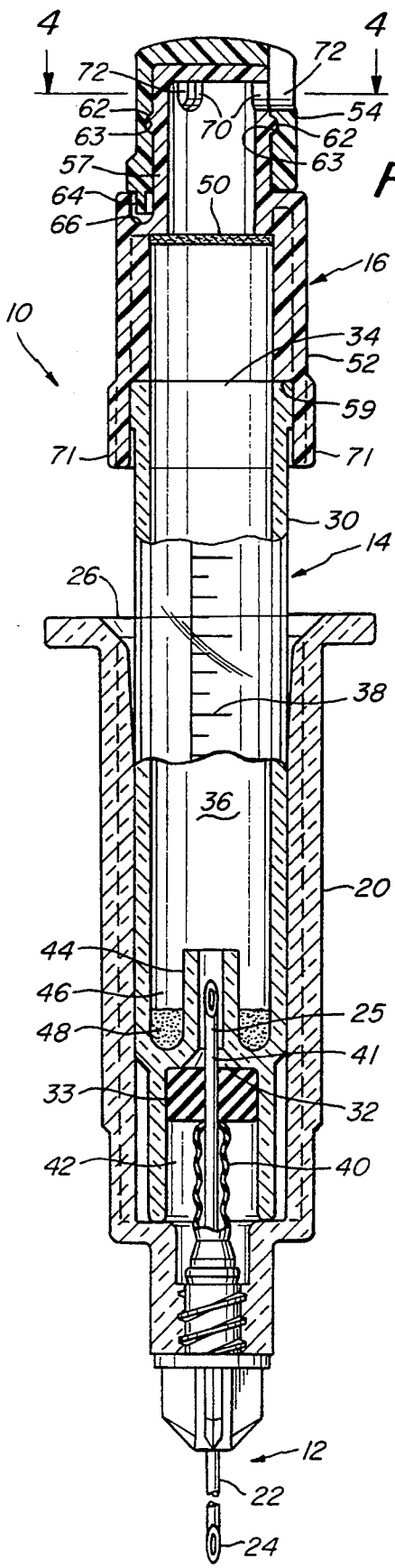
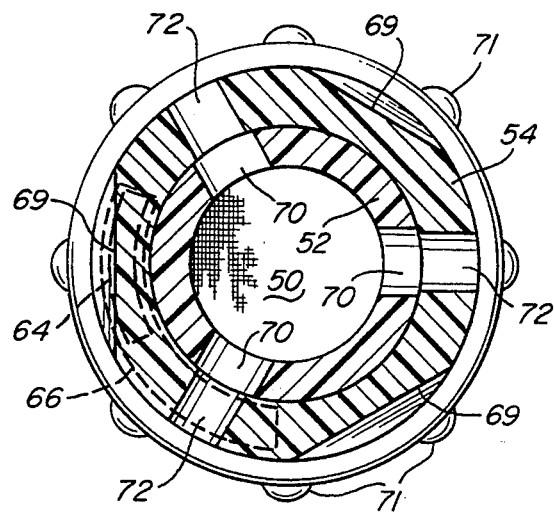
Fig. 3
Fig. 4

LIQUID COLLECTION DEVICE

FIELD OF INVENTION

The present invention relates to a liquid collection device.

BACKGROUND OF THE INVENTION

Various devices have been proposed for collecting samples of liquid, particularly blood, for testing and analysis. Needle and syringe assemblies are known which rely on either the circulatory pressure of the patient's blood, or a vacuum created by retraction of a plunger, to draw the blood sample into the collection tube. Vacuum tubes have been substituted for the syringe component, most notably in the Vacutainer® device distributed by Becton Dickinson & Co. Devices employing capillary action to draw puddles of blood into a collection device also have been proposed.

The volume of blood to be collected by the phlebotomist will vary depending upon the ultimate analytical technique and testing equipment. Variable volume syringe assemblies have been proposed in which the plunger is retracted until the free volume in the syringe corresponds to the volume of blood to be withdrawn. However, changes in the desired sample size are difficult to register after blood flow has commenced. The prior art therefore lacks a simple and reliable technique for selectively collecting variable volumes of blood and other liquids.

Various additives may be included in a collection tube prior to introduction of a liquid of interest. For example, it is known to have in place a coating, powder or gel, such as a gel separation barrier, in a blood collection tube to facilitate downline testing or analysis. In certain syringe type devices, an additive may impede flow of blood through the inlet or interfere with venting of the tube interior to the outside.

Various syringe type collection devices have been proposed which use the same opening to collect and dispense the liquid sample. Such devices limit the ability to pour off or pipette samples and provide little or no access to the collected liquid for introducing test specific additives.

SUMMARY OF THE INVENTION

The present invention is a device for accurately and safely collecting variable or, alternatively, pre-determined volumes of liquid, such as blood, for testing and analysis. The collection system prevents overflow of the collected liquid, alleviating the health risk posed by leakage during the collection procedure, downline handling and treatment. The device provides ready access to the collected liquids, facilitating setup and analysis in associated instruments.

The collection device is particularly suited to the microsampling of blood by venipuncture or capillary techniques. In a venipuncture system, a needle conducts blood from the patient's vein or artery directly into the collection device. In a capillary system, droplets from a small pool of blood are attracted into a collection tube by the capillary affect of a small diameter inlet. While microsampling of blood (less than 2 ml) is particularly contemplated by the present invention, larger volume collection devices are also within the scope of the invention.

In one embodiment of the invention, the device includes an elongated collection tube having an inlet for receiving a liquid, an outlet for venting the tube interior and a rotatable cap for sealing the collection tube, preventing blood overflow. A needle assembly may be coupled to the collection tube or the collection tube may be constructed and arranged to draw liquid through capillary forces.

In another embodiment of the invention, the collection device includes a tubular member which projects into the tube interior and which defines, together with the tube sidewall, an annular sump or reservoir. A test specific additive is held in the annular reservoir, out of the path of the inflowing liquid.

In another embodiment of the invention, a cap is removably mounted to the collection tube and includes a filter which allows passage of air and gas from the tube interior but prevents overflow of the collecting liquid. Uncoupling the cap from the collection tube permits selective pipetting of the liquid or introduction of additives or testing instrumentation into the filled tube.

It is among the general objects of the invention to provide a collection device in which the incidence of fluid overflow is greatly reduced.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which:

FIG. 3 is a sectional view of the fully assembled venipuncture collection system;

FIG. 4 is a sectional illustration along line 4—4 of the venipuncture collection system illustrated in FIG. 3;

DESCRIPTION OF THE PREFERRED EMBODIMENTS

Figure 1:
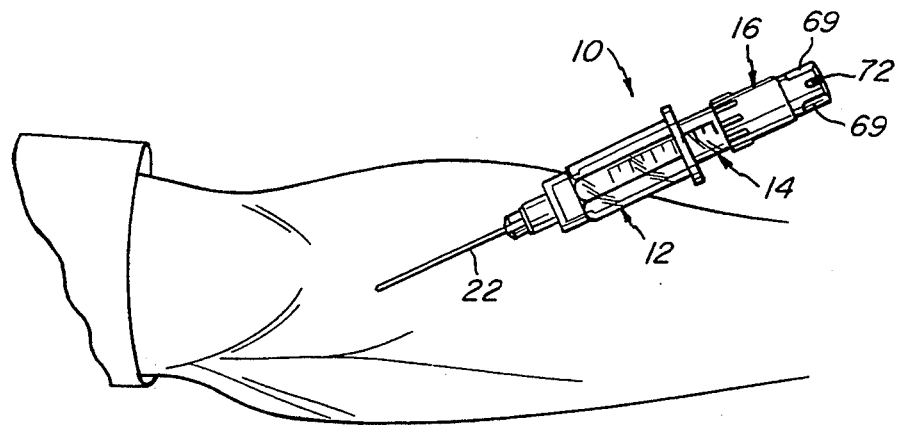
FIGS. 1–2 illustrate the use of a venipuncture collection device.
Figure 2:
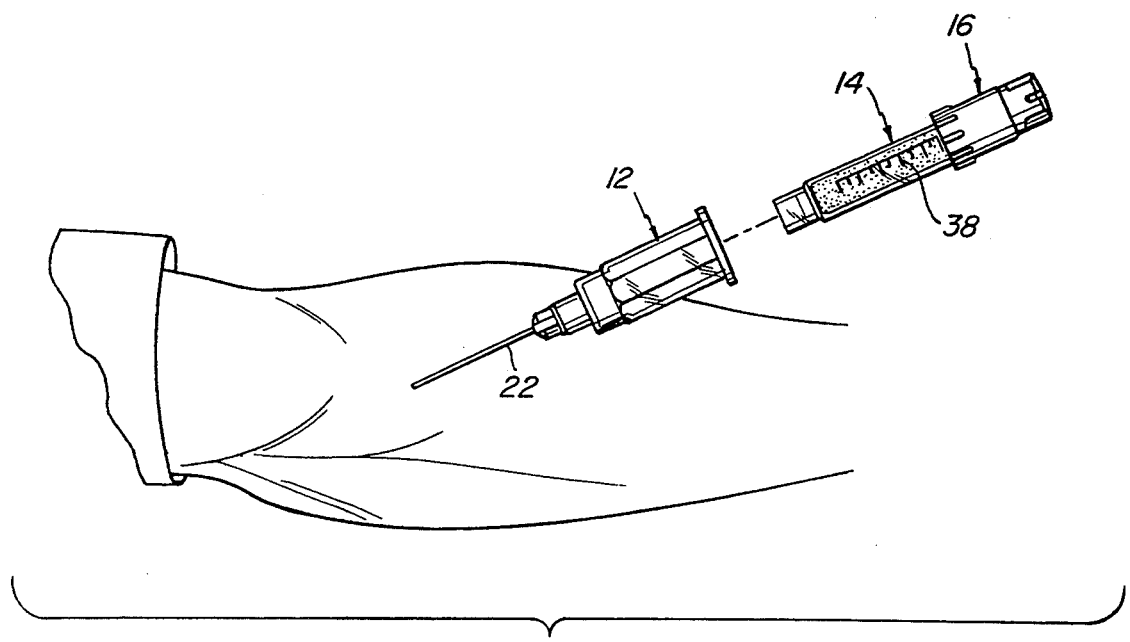

A collection device 10 for use in a venipuncture system is illustrated in FIGS. 1–2 and includes a needle assembly 12, a collection tube 14 and a valve cap 16. After tapping the vein or artery, blood is forced by circulatory pressure, with or without the assistance of a vacuum source (not shown), through the needle assembly 12 and into the collection tube 14. In the arrangement illustrated, the flow of blood is regulated by the displacement of air from the tube through vent openings in the cap 16. Blood flow into the collection tube cannot occur when the vent is closed, and air cannot escape, but will ensue so long as air exhausts through the vent. When a sufficient volume of blood has been collected, the cap is closed, sealing the vent and halting further blood flow. The tube 14 then may be removed from the needle assembly and the collected contents subjected to analysis and testing. A cap (not shown)

may be snap fitted over the inlet to further guard against blood loss during handling of the collection tube.

The needle assembly 12 illustrated in FIG. 3 includes a housing 20, which holds the collection tube, and a double-ended needle 22 with a pointed end 24 for piercing the patient's skin and a sheathed opposite end 25 for communicating with the collection tube interior. The proximal end of the housing 26 may be outwardly tapered, or include a slight chamfer, to encourage mating of the collection tube and needle assembly. The collection tube 14 includes an elongated transparent plastic tube 30 having an inlet 32 for receiving the collecting blood, an outlet 34 for venting air and blood gas from the tube interior, and a chamber 36 for holding the collecting blood. A self-sealing gasket 33 may be provided to prevent air or liquid leaks through the inlet when the device is used with a removable needle assembly such as is shown in FIG. 3. Indicia 38 on the surface of the tube indicates gradients of volume, allowing the phlebotomist accurately to collect varying volumes of blood with a single device.

The collection tube and needle assembly are removably attached by advancing the collection tube 14 against the sheathed end 25 of the needle, collapsing the sheath 40 as the underlying cannula 41 penetrates the self-sealing septum 33 and enters the collection tube 14. The retracted sheath 40 and the self-sealing septum 33 provide a leak-tight seal about the inlet, preventing air or blood leakage during collection. The elastic septum 33 automatically reseals the inlet when the needle is withdrawn from the collection tube, preventing loss or contamination of the collected liquids. Upon removal of the filled collection tube, the sheath 40 reverts to its original configuration, preventing the patient's blood from rising through the cannula opening. A leak preventive arrangement also may be provided by forming a counterbore in the inlet which engages and axially compresses the sheath when the needle is inserted into the collection tube. The compressed sheath fills the counterbore, sealing the cannula and inlet.

The collection tube 14 may include a chamber 42 which extends proximally of the inlet to accommodate the collapsed sheath and septum when the tube is completely engaged to the needle assembly. The proximal chamber may be eliminated if the sheath and septum are not utilized or may be reduced in size if the device includes only one of the leak preventive elements.

The collection tube may include a conduit 44 which projects into the container interior and defines, together with the container sidewalls, an annular reservoir 46 for placement of blood additives 48 such as a gel separation barrier. The cannula is received in the conduit when the tube and needle assembly are mated, so that blood is conducted into the collection tube proximal of the annular reservoir, preventing the blood additive from impeding the blood flow into the tube or clogging the cannula tip.

The use of a separable needle assembly and collection tube such as is shown in FIGS. 1-3 allows the phlebotomist to collect several vials of blood with a single puncture of the patient's vein or artery. The present invention also contemplates an integral collection tube and needle (single or double ended) device, eliminating the need for the holder, septum and sheath required for the separable device.

The valve cap 16 may be integral with the collection tube or, preferably, snap fitted about the outlet. Other arrangements for joining the cap and collection tube, such as by threading the components together, also are contemplated. The cap includes a hydrophobic filter 50, such as a 0.2 micron mesh filter, which extends above the outlet at the top of the collection tube, allowing passage of air and blood gases but preventing overflow of blood and other body liquids. The cap and filter may be attached by fitting the filter into a groove in the cap body, bonding the components with an adhesive or by ultrasonic welding or by insert molding the filter to the cap.

A plurality of ports 70, 72 in the cap 16 are selectively alignable, allowing gas from the collection tube 14 to exhaust to the outside, venting the tube interior. Rotating the cap clockwise or counterclockwise places the ports into and out of registry, allowing the user to vent or seal the collection tube at his or her election. In the open or vent position, blood flows into the collection tube. In the closed position, the greater air pressure within the collection tube prevents further blood from flowing into the tube. The location of the ports primarily along the side of the cap, as opposed to the end of the cap, allows a phlebotomist to grasp the device in the conventional manner with a thumb pressed against the tube end without occluding the vent ports. Fingerholds 69 may be molded into the surface of the cap to facilitate grasping and turning of the cap by the phlebotomist.

The valve cap includes an inner body 52 which is snap fitted to the outlet end of the collection tube, providing an extension of the collection tube, and a closed end outer body 54 which is rotatably mounted to the inner body. An interior shoulder 59 seats against the top of the collection tube further stabilizing the cap and tube. A pedestal portion 57 of the inner body extends above the outlet and includes an annular rib 62 which is positioned within a complementary groove 63 in the outer cap, allowing rotational movement between the two cap bodies. The outer body includes a partial circumferential rim 64 which is mated to a slot 66 in the inner body, limiting the relative rotation of the outer body between a position when the tube interior is vented and when the tube interior is sealed.

Alignment of the exhaust vents 70, 72 in the inner and outer bodies allows air in the collection tube interior to bleed to the outside as blood collects in the tube interior. The vents are spaced circumferentially about the cap so that ventilation occurs even when the phlebotomist fingers are covering the end or a sidewall portion of the cap.

The vents 70, 72 are aligned simply by rotating the cap outer body relative to the inner body. The cap remains in the "open" position or the "closed" position until the orientation is changed, obviating the need for the phlebotomist to hold the cap open to collect blood and the attendant risk that blood flow will be interrupted by improper user technique. The stop limit arrangement of the rim 64 and groove 66 assists the phlebotomist to completely align the corresponding vent openings.

The cap, when in the closed position, prevents blood overflow and therefore acts as a back-up for the hydrophobic filter. Provided a safe and careful technique is employed, selective manipulation of the valve cap may be used to regulate flow of blood into the collection tube. Rotating the outer body so that the vents 70, 72 are aligned permits blood to collect while the reverse rotation of the outer body so that the vents are no longer in communication stops the incoming flow of blood. It is contemplated that variable volumes of blood may be collected in a single collection device by rotating the cap into the open position, allowing blood to rise into the tube, monitoring the level of blood in the tube against indicia on the tube until a desired volume is reached, then stopping further inflow of blood by reversibly rotating the cap until the vents are no longer in communication.

After the desired volume of blood has been collected, the cap is rotated to the closed position and the collection tube is removed from the holder. A cap may be placed over the inlet to prevent leakage of the filled tube during handling. The valve cap and filter may be removed by snapping the inner body off of the collection tube, allowing ready access to a pipette or other means of adding additives or other materials to the collected liquids, to draw off liquid or to pour the liquid into a sample holder associated with the desired testing and analysis. Ribs 71 which are spaced circumferentially about the inner body facilitate grasping and removal of the cap.

A representative embodiment of the venipuncture collection device includes a needle holder formed of high density polyethylene and having a length of 1.70 inches and an inner diameter of 0.364 inches at the open end to 0.358 proximate the needle, stepping down to 0.238 immediately adjacent the threaded portion which is coupled to the needle. The collection tube is formed of K-resin and has a length of 2.050 inches and has an outer diameter at its major portion of 0.367 inches, ensuring a frictional fit with the needle assembly housing. The outlet end of the tube has an outer diameter of 0.399 inches. The reduced diameter proximal chamber which contains the septum and the collapsed sheath when the tube and needle assembly are engaged, has a length of 0.400 inches, an outer diameter of 0.304 inches and an inner diameter of 0.227 inches. The inwardly projecting conduit extends from the proximal chamber, and has a length of 0.300 inches and an inner diameter of 0.055 inches. The cap is made of polypropylene and includes an inner body having a length of 0.960 inches with a lower portion being 0.650 inches long and a pedestal portion being 0.310 inches long. The lower portion has an inner diameter of 0.395 inches which ensures a frictional fit with the vent end of the collection tube. The pedestal has an outer diameter of 0.290 inches which permits rotatable engagement with the 0.298 inch inner diameter outer body. The annular rib in the pedestal is 0.048 inches thick and has a diameter of 0.322 inches which fits into the outer body groove having an outer diameter of 0.329 and a groove dimension of 0.051 inches.

Figure 5A:
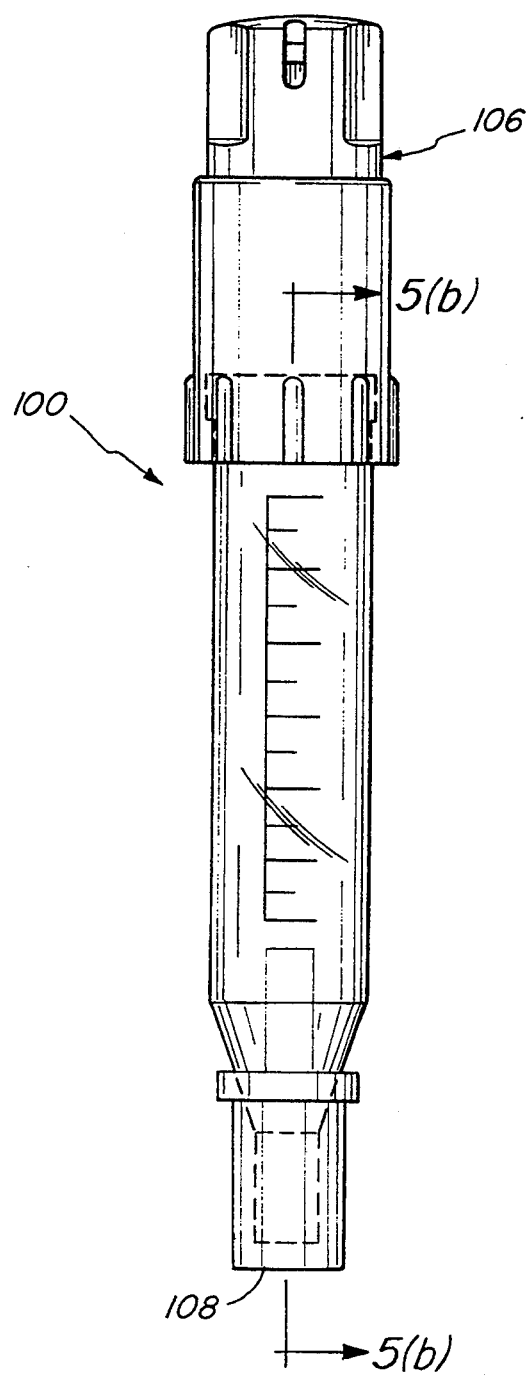
FIG. 5(a) is an illustration of a capillary collection device.
Figure 5B:
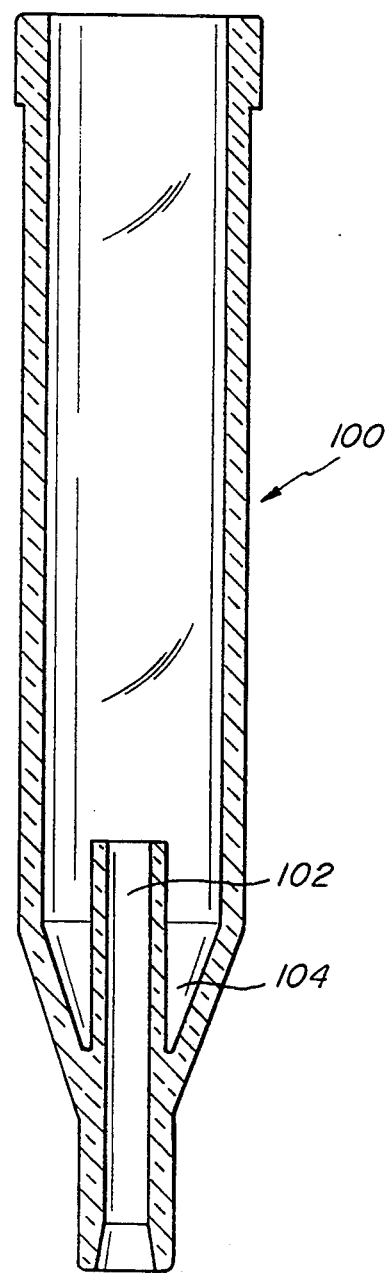
FIG. 5(b) is a sectional illustration along line 5(b)—5(b) of the capillary collection device illustrated in FIG. 5(a).

The capillary collection system 100, illustrated in FIGS. 5(a)–5(b), is similar to the venipuncture system. The principal differences are that the capillary system does not include the needle assembly, or the associated self-sealing septum and proximal chamber, but is provided with a narrower inlet opening 102 to ensure that droplets are drawn into the tube by capillary action. The capillary system also includes an annular reservoir 104 for holding blood additives and a rotatable cap 106 for selectively venting the collection tube. Additionally, a closure cap 108 may be provided which snap fits over the inlet after the tube is filled, ensuring safe handling during transport and testing. The operation of the capillary system is similar to the venipuncture system. The cap 106 is rotated into the open position, placing the tube interior and the ambient environment in communication. Air in the tube interior is displaced through the valve cap as droplets are drawn by capillary force into the device. Closing of the cap causes a pressure increase in the tube which exceeds the pressure of the capillary flow, preventing further blood from migrating into the device. Selective opening and closing of the valve cap permits the phlebotomist to collect varying volumes of blood from the patient.

A representative capillary device includes a collection tube formed of K-resin having an overall length of 2.050 inches. The inlet and the inward projection have a diameter of 0.075 inches and a length of approximately 0.700 inches. A slight chamfer at the inlet tip provides an enlarged diameter of 0.080 inches. The vent end of the collection tube has an outer diameter of 0.399 inches which mates with a valve cap similarly sized to the cap described in the representative embodiment of the venipuncture system.

The present invention therefore provides a collection device, amongst which are certain of the following advantages. A collection tube with a rotatable valve cap for selectively venting the collection tube interior. A removable cap and hydrophobic filter assembly rendering the collected blood accessible to a pipette or probe, and allowing the sample liquid to be poured off directly into testing apparatus. Also, a collection tube having blood additives in a depressed reservoir in the inlet end of the collection tube, allowing unimpeded flow of blood into the device.

It should be understood that the foregoing description of the invention is intended merely to be illustrative thereof and that other equivalents and modifications of the invention may be apparent to those skilled in the art.

What is claimed is:

1. A liquid collection device, comprising;
   a liquid collection tube defining a chamber for receiving a liquid, and having an inlet which receives the liquid to be collected and an outlet through which a gas in said chamber may be exhausted to the outside of said chamber;
   a valve supported by said liquid collection tube and including at least one vent, said valve being rotatable between a first position when said vent is in communication with said chamber and the outside and a second position when said vent is not in communication with said chamber and the outside.

2. A liquid collection device, comprising:
   a liquid collection tube defining a chamber for receiving a liquid, and having an inlet which receives the liquid to be collected and an outlet through which a gas in said chamber may be exhausted to the outside of said chamber;
   a cap rotatably mounted to said collection tube and having at least one vent which is communicable between said outlet and the outside, said cap being rotatable between a first open position when said at least one vent is in communication with said outlet and the outside and a second position when said at least one vent is not in communication with said outlet and the outside.

3. The liquid collection device recited in claim 2 wherein said rotatable cap includes a first body mounted to said collection tube and a second body rotatably mounted to said first body, each of said first body and said second body including at least one vent which are alignable by rotation of said second body.

4. The liquid collection device recited in claim 3 wherein said first body includes one of a mated rim and groove for limiting rotation of said cap and said second body includes said other of said mated rim and groove.

5. The liquid collection device recited in claim 2 wherein said at least one vent extends through a side wall and an end wall portion of said cap.

6. The liquid collection device recited in claim 2 wherein said cap is removably mounted to said collection tube.

7. The liquid collection device recited in claim 2 further comprising a needle connected to said collection tube.

8. The liquid collection device recited in claim 2 wherein said inlet is constructed and arranged to draw liquid into the collection tube through capillary action.

9. A liquid collection device, comprising:
an elongated liquid collection tube defining a chamber for collecting a liquid, having an inlet which receives the liquid to be collected and an outlet through which a gas in said chamber may be exhausted, and including a tubular member projecting into said chamber which is in communication with said inlet;
an annular reservoir defined by said tubular member and said collection tube, and an additive being contained within said annular reservoir;
a rotatable valve cap including a first body and a second body, said first body being removably mounted to said collection tube and said second body being rotatably mounted to said first body, each of said first body and said second body including at least one vent which are alignable by rotation of said second body; and
a hydrophobic filter supported by said cap between said outlet and said at least one vents.

10. A liquid collection device, comprising:
an elongated liquid collection tube defining a chamber for collecting a liquid, having an inlet which receives the liquid to be collected and an outlet through which a gas in said chamber may be conducted to the outside of said chamber;
said elongated liquid collection tube having at least one vent through which gas conducted from said outlet may exhaust to the outside; and
a sealing member rotatable between a first position when said at least one vent is in communication between said outlet and the outside and a second position when said at least one vent is not in communication between said outlet and the outside.

11. A liquid collection device, comprising:
an elongated liquid collection tube defining a chamber for collecting a liquid, having an inlet which receives the liquid to be collected and an outlet through which a gas in said chamber may be exhausted;
a rotatable valve cap including a first body and a second body, said first body being removably mounted to said collection tube and said second body being rotatably mounted to said first body, each of said first body and said second body including at least one vent which are alignable by rotation of said second body; and
a hydrophobic filter supported by said cap between said outlet and said alignable vents.

12. A liquid collection device, comprising:
a liquid collection tube defining a chamber for receiving a liquid, and having an inlet which receives the liquid to be collected and an outlet through which a gas in the chamber may be exhausted; and
a cap removably mounted to said collection tube and having at least one vent, said cap further including a filter positioned between said outlet and said at least one vent which is resistant to the passage of liquid but not of the chamber gas, wherein said removably mounted cap includes two pieces, at least one of which is movable relative to the other, one of said two pieces being removably coupled to said collection tube, wherein said two pieces are movable between a first position in which a gas may be exhausted from said chamber through said vent, and a second position in which a gas may not be exhausted from said chamber through said vent.

13. The liquid collection device recited in claim 12 wherein said filter is a hydrophobic filter.

14. The liquid collection device recited in claim 12 wherein said removably mounted cap is snap fit over said outlet of said liquid collection tube.

15. The liquid collection device recited in claim 12 wherein said removably mounted cap has a plurality of vents.

* * * * *